(12) United States Patent
Mitchell et al.

(10) Patent No.: US 9,456,868 B2
(45) Date of Patent: Oct. 4, 2016

(54) FLEXIBLE PROBE WITH ADJUSTABLE TIP

(71) Applicant: Smith & Nephew, Inc., Memphis, TN (US)

(72) Inventors: Mathew Erle Mitchell, Pelham, NH (US); Christopher D. McDonald, Newburyport, MA (US); Paul Robert Duhamel, Groton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/673,956

(22) Filed: Mar. 31, 2015

(65) Prior Publication Data

US 2015/0202001 A1 Jul. 23, 2015

Related U.S. Application Data

(62) Division of application No. 13/490,665, filed on Jun. 7, 2012, now Pat. No. 9,011,429.

(51) Int. Cl.
| | |
|---|---|
| *A61B 18/14* | (2006.01) |
| *A61B 17/32* | (2006.01) |
| *A61B 18/00* | (2006.01) |
| *A61B 17/00* | (2006.01) |

(52) U.S. Cl.
CPC ... *A61B 18/1492* (2013.01); *A61B 17/320016* (2013.01); *A61B 18/148* (2013.01); *A61B 2017/003* (2013.01); *A61B 2017/00309* (2013.01); *A61B 2017/00318* (2013.01); *A61B 2017/00323* (2013.01); *A61B 2018/00196* (2013.01); *A61B 2018/00202* (2013.01)

(58) Field of Classification Search
CPC .................. A61B 18/1492; A61B 17/320016; A61B 18/148; A61B 2017/003; A61B 2017/00309; A61B 2017/00318; A61B 2017/00323; A61B 2018/00196; A61B 2018/00202
See application file for complete search history.

(56) References Cited

U.S. PATENT DOCUMENTS

| | | | | |
|---|---|---|---|---|
| 5,389,073 | A | * | 2/1995 | Imran ................ A61B 18/1492 600/435 |
| 5,715,817 | A | * | 2/1998 | Stevens-Wright . A61B 18/1492 600/373 |
| 2006/0020287 | A1 | * | 1/2006 | Lee ...................... A61B 17/062 606/205 |
| 2010/0081864 | A1 | * | 4/2010 | Hess ................ A61B 17/00234 600/37 |

* cited by examiner

*Primary Examiner* — Catherine Voorhees (57) ABSTRACT

An instrument includes a handle portion, an actuator, a shaft, a rigid member, and an angular control mechanism. The shaft has a proximal end and a distal end with an electrode region, and a flexible region in between. Moving the actuator causes portions of the flexible region distal of a pivot region to bend such that an angular orientation and a radial offset of the electrode region reach an angular orientation and a radial offset, respectively, when the actuator reaches the end position. A distal portion of the rigid member defines the pivot region. Moving the rigid member along the shaft causes the pivot region to translate. The radial offset varies depending on the position of the pivot region.

8 Claims, 6 Drawing Sheets

FLEXIBLE PROBE WITH ADJUSTABLE TIP

CROSS-REFERENCE TO RELATED APPLICATIONS

This application is a divisional of U.S. patent application Ser. No. 13/490,665, filed Jun. 7, 2012, the disclosure of which is incorporated by reference in its entirety.

TECHNICAL FIELD

This document relates to a flexible probe with an adjustable tip.

BACKGROUND

During arthroscopic surgery, limited portal positions and tight spaces near a surgical site can restrict access into and around the surgical site. An arthroscopic device with an actively flexing tip can reach areas within a patient's body that may be difficult to reach with a device having a more rigid tip.

SUMMARY

According to one aspect, an instrument includes a handle portion, an actuator movably coupled to the handle portion, a shaft having a proximal end coupled to the handle portion and the actuator, a rigid member, and an angular control mechanism. The actuator is configured to move between a start position and an end position. The shaft has a distal end that includes an electrode region, and a flexible region between the proximal and distal ends. A movement of the actuator causes portions of the flexible region positioned distally of a pivot region to bend such that both an angular orientation and a radial offset of the electrode region relative to an axis of the shaft increase as the actuator approaches the end position and reach a maximum angular orientation and a maximum radial offset, respectively, when the actuator reaches the end position, the pivot region being positioned along a length of the shaft. The rigid member has a proximal portion and a distal portion and is movably coupled to the shaft such that the distal portion of the rigid member defines the pivot region. Movement of a position of the rigid member along the length of the shaft causes a position of the pivot region to translate axially along the length of the shaft. The maximum radial offset varies depending on the position of the pivot region along the length of the shaft. The angular control mechanism is configured to control the angular orientation of the electrode region such that the maximum angular orientation is substantially the same regardless of the position of the rigid member along the length of the shaft.

Implementations of this aspect may include one or more of the following features. For example, the instrument may further include a pull wire having a proximal portion and a distal portion. The proximal portion of the pull wire may be coupled to the actuator, and the distal portion of the pull wire may be coupled to the shaft. The movement of the actuator may cause the pull wire to be pulled such that the portions of the flexible region of the shaft positioned distal of the pivot region bends. The actuator may include at least one of a slide, a lever, or a dial. The angular control mechanism may include a pivot control element movably coupled to the handle portion. The proximal portion of the rigid member may be coupled to the pivot control element such that a movement of the pivot control element causes the rigid member to translate axially along the length of the shaft. The pivot control element and the actuator may be mechanically linked such that the pivot control element adjusts the end position of the actuator such that the maximum angular orientation is substantially the same regardless of the position of the rigid member along the length of the shaft. The pivot control element may include at least one of a slide, a lever, or a dial. The maximum angular orientation of the electrode region relative to the shaft axis may be 110 degrees. The flexible region may include flex cuts along the length of the shaft. The rigid member may include an outer tube that slides over the shaft. The rigid member may include an inner tube that slides within the shaft. The distal end of the rigid member may include flex cuts along a length of the rigid member. The instrument may further include a shaft rotation mechanism. A movement of the shaft rotation mechanism may cause the shaft to rotate about the shaft axis.

According to another aspect, an instrument includes a handle portion, a shaft having a proximal end coupled to the handle portion, and a first pull wire coupled distally to the shaft at a first site and a second pull wire coupled distally to the shaft at a second site different from the first site. The shaft has a distal end that includes an electrode region, and a flexible region between the proximal and distal ends. Pulling the first pull wire causes portions of the flexible region of the shaft positioned distally of a pivot region to bend such that the electrode region has a first radial offset. Pulling the second pull wire causes portions of the flexible region of the shaft positioned distally of the pivot region to bend such that the electrode region has a second radial offset different from the first radial offset.

Implementations of this aspect may include one or more of the following features. For example, a maximum angular orientation of the electrode region having the first radial offset may be substantially equal to the maximum angular orientation of the electrode region having the second radial offset.

According to another aspect, a method of controlling a shaft of an instrument includes moving the actuator such that a distal end of the shaft bends to a first maximum angular orientation and a first maximum radial offset, translating a position of the pivot region, and after translating the position of the pivot region, moving the actuator such that the distal end of the shaft bends to a second maximum angular orientation and a second maximum radial offset. The shaft includes a flexible region and is coupled proximally to an actuator. A movement of the actuator causes portions of the flexible region positioned distal of a pivot region to bend. The first and second maximum angular orientations are substantially equal and the first and second maximum radial offsets are different.

Implementations of this aspect may include one or more of the following features. For example, translating the position of the pivot region may include translating a rigid member axially along the length of the shaft. Translating the position of the pivot region to a first pivot position may restrict the actuator from moving beyond the first end position. Translating the position of the pivot region to a second pivot position may restrict the actuator from moving beyond the second end position. The method may further include moving a pivot control element to translate the position of the pivot region by translating a rigid member disposed axially along the shaft and to adjust an end point of the actuator to correspond to the substantially equal maximum angular orientation of the distal end of the shaft. Moving the actuator may cause a pull wire to be pulled, the pull wire being coupled proximally to the actuator and distally to the shaft, such that pulling the pull wire causes the distal end of the shaft to bend. The method may further include rotating the shaft about an axis of the shaft.

The details of one or more implementations are set forth in the accompanying drawings and the description below. Other features, aspects, and advantages will become apparent from the description, the drawings, and the claims.

DETAILED DESCRIPTION

A surgical probe, such as an arthroscopic probe, can include an actively flexible tip that delivers energy, such as RF energy, to a surgical site. When the tip of the surgical probe flexes or bends, the tip can reach a maximum height and a maximum angular orientation relative to a shaft of the probe. In some implementations, the maximum height can be changed without changing the maximum angular orientation.

Figure 1A:
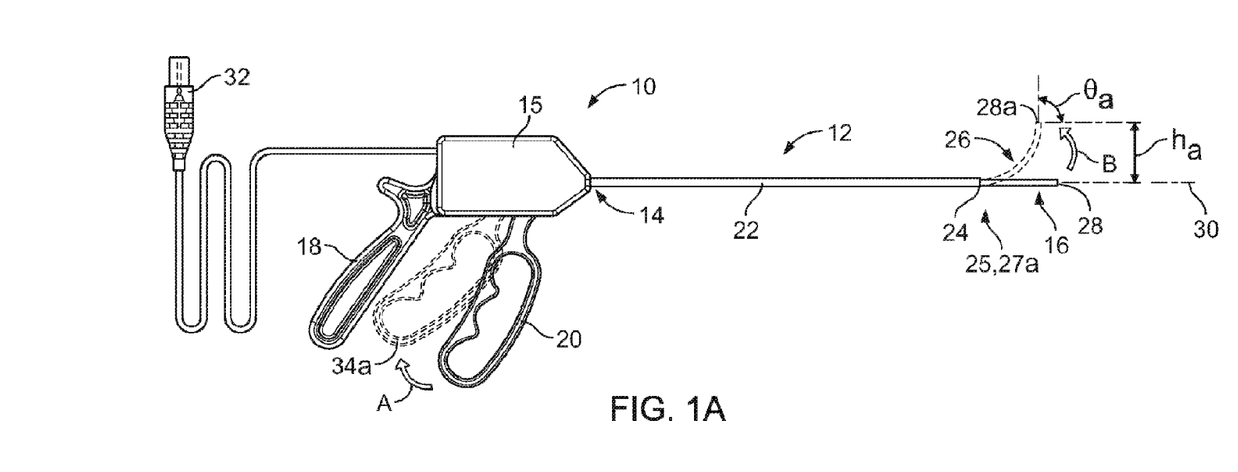
FIGS. 1A and 1B are side views of a probe with a flexible shaft.
Figure 1B:
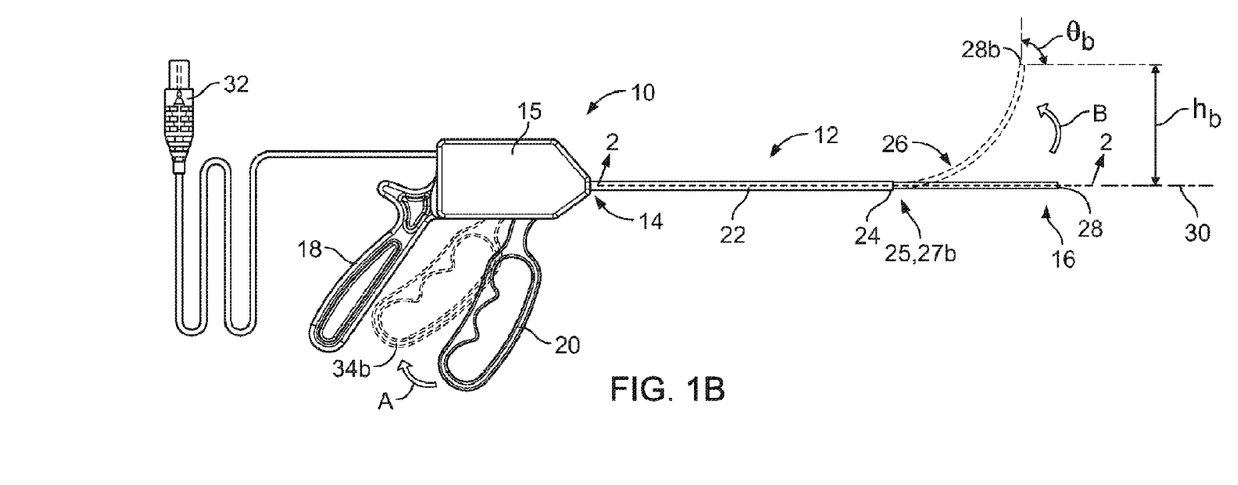

Referring to FIGS. 1A and 1B, a probe 10 includes a shaft 12 having a proximal end 14 and a distal end 16. The shaft 12 is coupled at its proximal end 14 to a probe body 15, and the body 15 includes a stationary handle portion 18 that is generally shaped to conform to a user's hand. The body 15 also includes an actuator 20 that can be moved by the user, for example, in a direction indicated by arrow A, to bend the distal end 16 of the shaft 12 in a direction indicated by arrow B. A maximum height, or radial offset, attained by a maximally bent distal end 16 can be changed as discussed further below. Additionally, as discussed further below, the probe 10 includes an angular control mechanism that allows the distal end 16 of the shaft 12 to attain a substantially constant maximum angular orientation, $\Theta_a$, $\Theta_b$, regardless of a maximum radial offset, $h_a$, $h_b$, of the distal end 16.

In particular, the shaft 12 of the probe 10 includes a rigid member, such as a rigid sleeve 22, that slidably couples to the shaft 12 and enhances a rigidity of the shaft 12 at portions that come in contact with the rigid member. The rigid sleeve 22, and other implementations of the rigid member as discussed further below, can translate axially along a length of the shaft 12 to translate a pivot region of the shaft 12. For example, as shown in FIGS. 1A and 1B, a distal portion 24 of the rigid sleeve 22 defines a pivot region 25 at which the shaft 12 begins to bend in response to a movement of the actuator 20. As such, the user, by translating the rigid sleeve 22 on the shaft 12 along a shaft axis 30, can change a position of the pivot region 25 along the length of the shaft 12 and thus vary how much of the shaft 12 bends or flexes in response to movement of the actuator 20. For example, FIG. 1A shows the pivot region 25 at a first position 27a, and FIG. 1B shows the pivot region 25 at a second position 27b. The shaft 12 includes a flexible region 26 positioned between the proximal and distal ends 14, 16 of the shaft 12 that enhances a flexibility of the shaft 12 in the region. The shaft 12 and the rigid sleeve 22 may be formed from any suitable biocompatible material including polymers, plastics, ceramics, metals, or combinations thereof.

The distal end 16 of the shaft 12 includes an electrode region 28 that can, for example, deliver energy to a surgical site within a patient's body. The energy delivered can include RF energy, electrical energy, mechanical energy, or the like that helps treat and/or diagnose the surgical site. Signals to and from the electrode region 28 can be provided through electrical connection 32 that connects to an external source/monitor (not shown).

Figure 2:
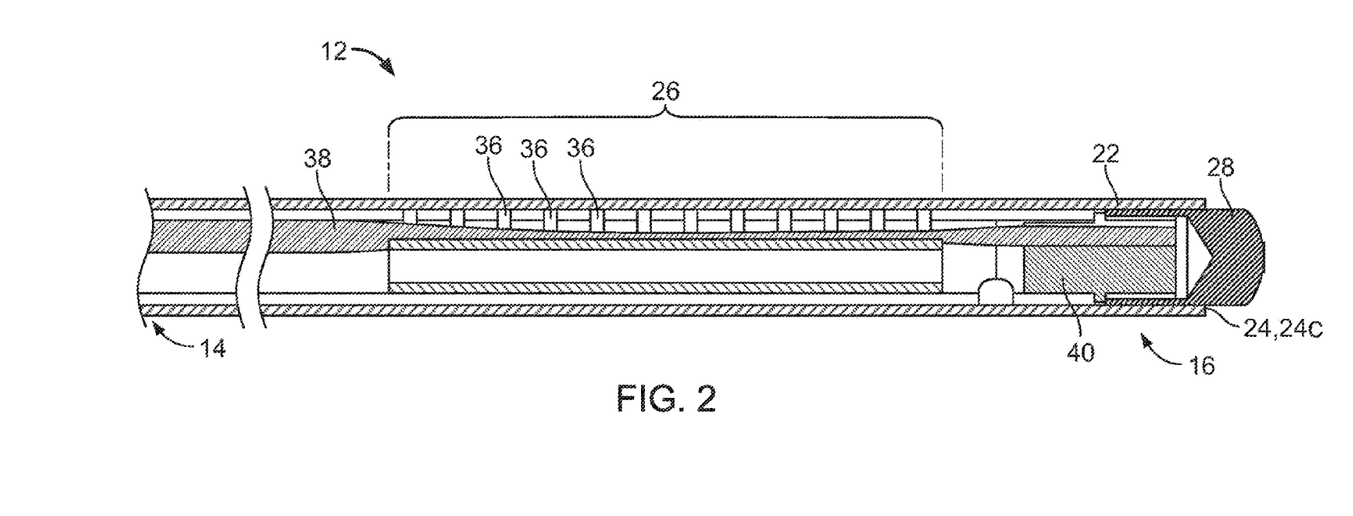
FIG. 2 is a partial side view of the flexible shaft of FIG. 1A.

When the user moves the actuator 20 in the direction of arrow A to an end position 34a, 34b, the electrode region 28 moves accordingly in response to the movement. For example, when the user moves the actuator 20 to the end position 34a, and when rigid sleeve 22 defines the pivot region 24a, the electrode region 28 moves to an end position 28a (FIG. 1A). Similarly, when the user moves the actuator 20 to the end position 34b, and when the rigid sleeve 22 defines the pivot region 24b, the electrode region 28 moves to an end position 28b (FIG. 1A). Accordingly, movement of the electrode region 28 to the end position 28a results in the electrode region 28 reaching the maximum angular orientation, $\Theta_a$, and the maximum radial offset, $h_a$, while movement of the electrode region 28 to the end position 28b results in the electrode region 28 reaching the maximum angular orientation, $\Theta_b$, and the maximum radial offset, $h_b$. As discussed further below, an angular control mechanism ensures that maximum angular orientations of the electrode region 28 are substantially constant regardless of the maximum radial offset that is attained. The maximum angular orientation of the electrode region 28 can be between about 90 and 110 degrees. In some cases, the maximum angular orientation can be greater than 110 degrees. Referring to FIG. 2, the flexible region 26 of the shaft 12 is positioned between the proximal and distal ends 14, 16. In some cases, the entire length of the shaft 12 may include the flexible region 26. As discussed, the flexible region 26 can help enhance the flexibility of the shaft 12 at portions of the shaft containing the flexible region 26. In some cases, portions of the shaft 12 that do not contain the flexible region 26 may still be flexible. Additionally, as seen in FIG. 2, the flexible region 26 can include one or more flex cuts 36 along one or more sides of the shaft 12 to improve bending of the shaft 12. The flex cut 36 can be in the form of a continuous spiral cut, interlocking cut, puzzle cut, or other appropriate cut arrangement that provides the shaft 12 with greater flexibility. Alternatively, or additionally, the flexible region 26 can include one or more materials that help increase flexibility. During use, as shown in FIG. 2, the rigid sleeve 22 can cover the entire length of the shaft 12, such that a pivot region 24c defined by the distal portion 24 of the sleeve 22 is positioned near the distal end 16 of the shaft 12. In some cases, and as discussed below, the rigid sleeve 22 can have portions that include flex cuts 36.

The shaft 12 can also house one or more steering or pull wires 38 that can be actuated by the actuator 20 (FIG. 1) to actively flex the distal end 16 of the shaft 12. For example, a proximal portion of the pull wire 38 can be coupled to the actuator 20, and a distal portion of the pull wire 38, which can terminate at a shaft connection block 40, can be coupled to the shaft 12. In use, when the user moves the actuator 20, the pull wire 38 is pulled such that portions of the shaft 12 positioned distal of the pivot region can flex in response to movement of the pull wire 38.

Figure 4A:
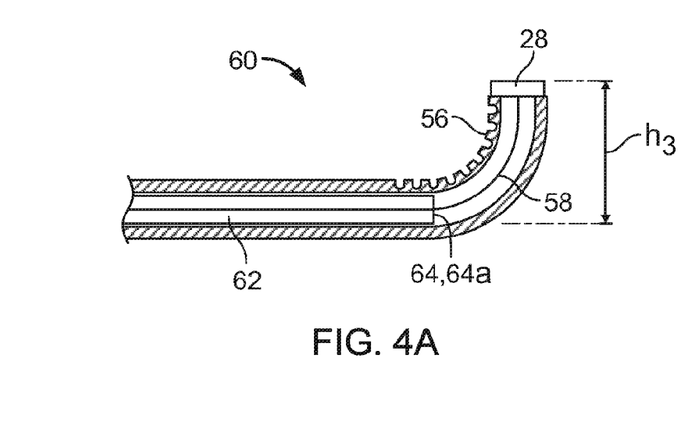
FIGS. 4A and 4B are partial side views of another alternative implementation of a flexible shaft.
Figure 4B:
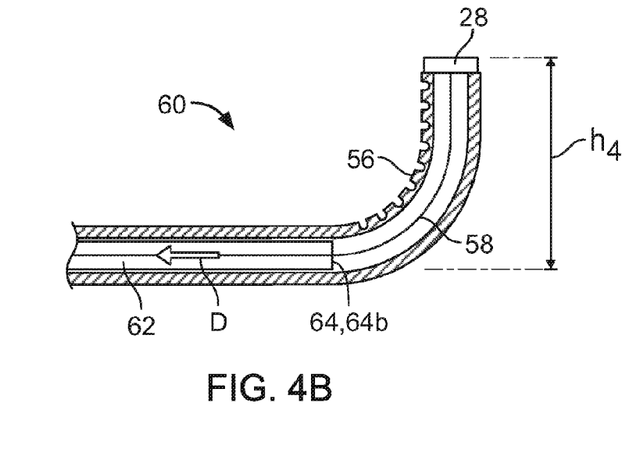
Figure 5:
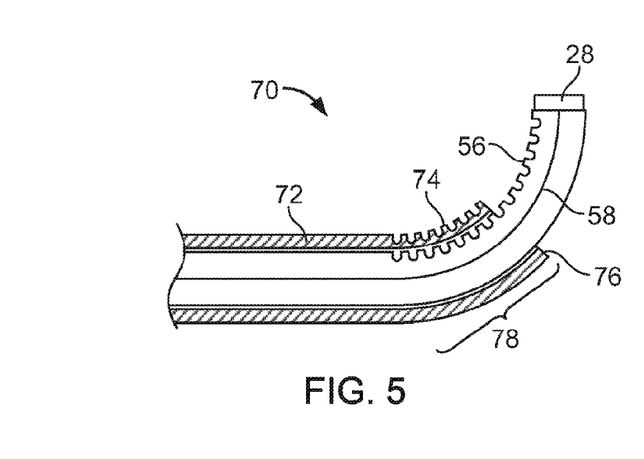
FIG. 5 is a partial side view of another alternative implementation of a flexible shaft.

FIGS. 3-5 show various implementations of the rigid member and the flexible shaft of FIGS. 1 and 2.

Figure 3A:
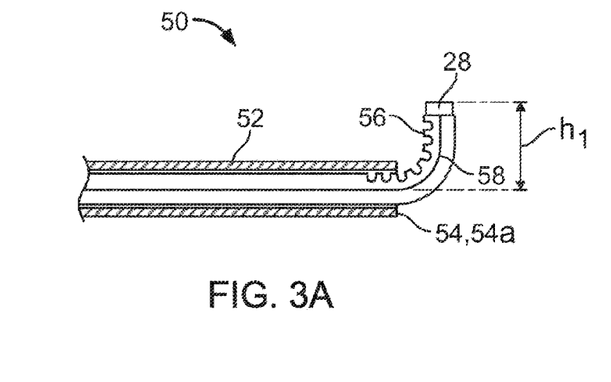
FIGS. 3A and 3B are partial side views of an alternative implementation of a flexible shaft.
Figure 3B:
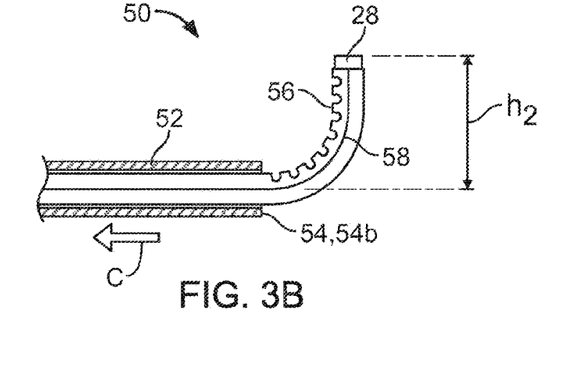

Referring to FIGS. 3A and 3B, a shaft 50 has a rigid outer member 52 that is slidably coupled to an outer portion of the shaft 50. A distal portion 54 of the outer member 52 defines a movable pivot region 54a, 54b along a length of the shaft 50. By axially translating the rigid outer member 52, for example, in a direction indicated by arrow C, a pivot region of the shaft 50 moves from the pivot region 54a to the pivot region 54b, thereby increasing a portion of the shaft 50 that flexes in response to movement of the actuator 20 (FIG. 1).

As described above with respect to FIG. 2, when the user moves the actuator 20, a pull wire 58 is pulled such that portions of the shaft 50 distal of the pivot region 54a, 54b bends. With the outer member 52 defining pivot regions 54a, 54b, the electrode region 28 can attain, respectively, maximum radial offsets, $h_1$, $h_2$. As described below, an angular control mechanism provides that the electrode region 28 always flexes to substantially a same maximum angle regardless of the position of the pivot region along the length of the shaft 50. Flex cuts 56 can improve the flexibility of the shaft 50.

Referring to FIGS. 4A and 4B, a shaft 60 has a rigid inner member 62 that is slidably coupled to an inner portion of the shaft 60. In some cases, the rigid inner member 62 can be an inner sleeve that contains the pull wire 58. Alternatively, the rigid inner member can be a rigid rod-like structure. A distal portion 64 of the inner member 62 defines a movable pivot region 64a, 64b along a length of the shaft 60. By axially translating the rigid inner member 62, for example, in a direction indicated by arrow D, a pivot region of the shaft 60 moves from the pivot region 64a to the pivot region 64b, thereby increasing a portion of the shaft 60 that flexes in response to movement of the actuator 20 (FIG. 1). As described above with respect to FIG. 3, the electrode region 28 can attain maximum radial offsets, $h_3$, $h_4$, with the inner member 62 defining, respectively, pivot regions 64a, 64b. An angular control mechanism provides that the electrode region 28 always flex to a same maximum angle regardless of the position of the pivot region along the length of the shaft 60.

Referring to FIG. 5, a shaft 70 includes a rigid outer member 72 having flex cuts 74 at a distal portion 76. Because flex cuts 74 can improve the flexibility of the outer member 72 at portions of the member 72 containing the flex cuts 74, portions of the rigid outer member 72 can bend in response to movement of the actuator 20 (FIG. 1). Instead of providing a sharp transition point from a rigid portion of the shaft 70 to a flexible portion, the flex cuts 74 provide a progressive pivot area 78 along a length of the member 72. Having the progressive pivot area 78 can, for example, reduce potential for stress concentrations at the pivot region and/or allow for a more uniform curvature of the shaft 70. Alternatively, or additionally, other structural or material variations along a portion of the outer member 72 can result in improved flexibility of the outer member 72. For example, all or portions of the outer member 72 can include pliable catheter tubing or other forms of flexible tubing. The rigid inner member 62 of the shaft 60 may also include flexible portions as described above with respect to outer member 72.

Figure 6A:
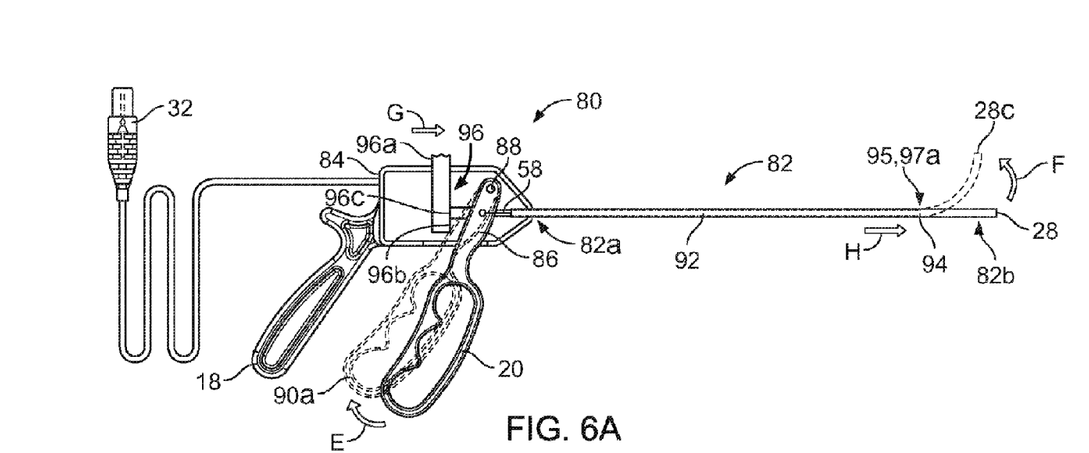
FIGS. 6A and 6B are side view of an alternative implementation of a probe with a flexible shaft.
Figure 6B:
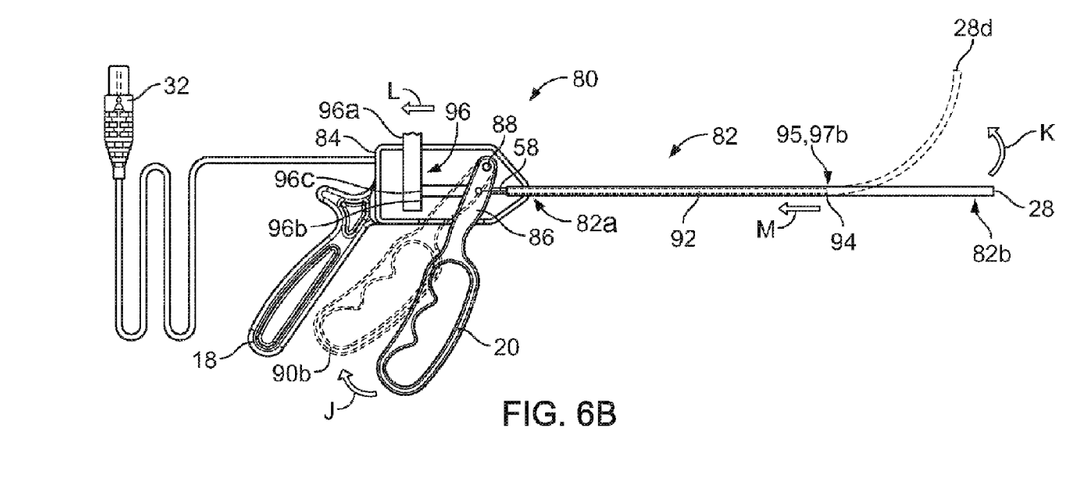

Referring to FIGS. 6A and 6B, a particular implementation of the probe 10 (FIG. 1) includes an angular control mechanism that can maintain an angle of the flexible tip by limiting actuation of the actuator 20. As shown, a probe 80 includes a shaft 82 having a proximal end 82a and a distal end 82b. The proximal end 82a of the shaft 82 is coupled to a probe body 84, and the body 84 includes an actuator 20. The actuator 20 can be a slide, lever, dial, or any other mechanical control element that couples to the shaft 82 and whose movement causes the distal end 82b of the shaft 82 to bend or flex accordingly. For example, the actuator 20 can include a lever portion 86 that is coupled to the pull wire 58 and is rotatably attached to the body 84 at a hinge point 88. In use, when the user moves the actuator 20 to pull back on the lever portion 86, the pull wire 58 is pulled such that portions of the shaft 82 can bend in response. For example, moving the actuator 20 in a direction indicated by arrows E and J causes the electrode region 28 to move in a direction indicated, respectively, by arrows F and K.

The shaft 82 has a rigid inner sleeve 92 that is slidably coupled to an inner surface of the shaft 82. A distal portion 94 of the inner member 92 defines a movable pivot region 95 along a length of the shaft 82. For example, FIG. 6A shows the pivot region 95 at a first position 97a, and FIG. 6B shows the pivot region 95 at a second position 97b. Alternatively, the shaft can have a rigid outer sleeve as described above with respect to FIG. 3. The pull wire 58 is disposed within the inner sleeve 92 and is coupled distally to an inner surface of the shaft 82. The proximal portion of the pull wire 58 is coupled to the lever portion 86 of the actuator 20, such that a movement of the actuator 20 pulls the pull wire 58 to actuate the electrode region 28.

The angular control mechanism, as mentioned above, can allow the electrode region 28 to attain a substantially constant maximum angular orientation regardless of the position of the pivot region. Various manual, mechanical, electrical, and/or electronic mechanisms may be utilized to provide the desired constant maximum angular orientation of the electrode region 28. For example, the probe 80 can have an angular control mechanism in the form of a pivot control element 96.

The pivot control element 96, as shown in FIGS. 6A and 6B, is a sliding element disposed within the body 84 of the probe 80. The pivot control element 96 is coupled to the inner sleeve 92 and includes a user control portion 96a and an actuator blocking portion 96b. In use, the pivot control element 96 can adjust an end position of the actuator 20 as described further below. The inner sleeve 92 and the pivot control element 96 are mechanically linked, for example via a connection portion 96c, such that a movement of the pivot control element 96 causes the inner sleeve 92, and thus a position of the pivot region 95 along the shaft 82, to translate. In use, the user can slide the user control portion 96a, for example, in a direction indicated arrow G, to translate the pivot region 95 to the position 97a as indicated by arrow H. Similarly, the user can slide the user control portion 96a in a direction indicated by arrow L to translate the pivot region 95 to the position 97b as indicated by arrow M.

A particular location of the pivot region along the shaft 82 generally determines how far the user must move the actuator 20 to move the electrode region 28 to reach the desired maximum angular orientation. For example, in FIG. 6A, the electrode region 28 reaches an end position 28c having the maximum angular orientation when the actuator 20 is moved to an end position 90a. Here, moving the actuator 20 past the end position 90a will cause the electrode region 28 to reach an angular orientation that is greater than the desired maximum angular orientation. Similarly, in FIG. 6B, the electrode region 28 reaches an end position 28d having the maximum angular orientation when the actuator 20 is moved to an end position 90b. Here, moving the actuator 20 to the end position 90a will result in the electrode region 28 reaching an angular orientation that is less than the desired maximum angular orientation.

The actuator blocking portion 96b of the pivot control element 96 can provide angular control of the electrode region 28 by mechanically blocking, for example, the movement of the actuator 20 when it has reached the end position 90a corresponding to the pivot position 97a and the end position 28c, or blocking the movement of the actuator 20 when it has reached the end position 90b corresponding to the pivot position 97b and the end position 28d. Shapes, configurations, and/or relative arrangements of the actuator blocking portion 96b and the lever arm 86 can be varied and fine-tuned to assure that the maximum angular orientation of the electrode region 28 is generally the same regardless of the location of the pivot region. In some cases, the maximum angular orientation of the electrode region 28 may be varied by the user before or during use of the probe 80. For example, sliding the pivot control element 96 while maintaining contact between the actuator blocking portion 96b and the lever arm 86 will generally change the radial offset of the electrode region 28 without changing its angular orientation.

Instead of using an element such as the actuator blocking portion 96b to physically limit the movement of the actuator 20, other implementations of the angular control mechanism may include visual, audio, and/or tactile feedback mechanisms that let the user know when the actuator 20 has reached a position corresponding to the desired movement of the electrode region 28. In some cases, the angular control mechanism may include electronic sensors and/or actuators for maintaining a constant maximum angular orientation of the electrode region 28.

Figures 7A, 7B:
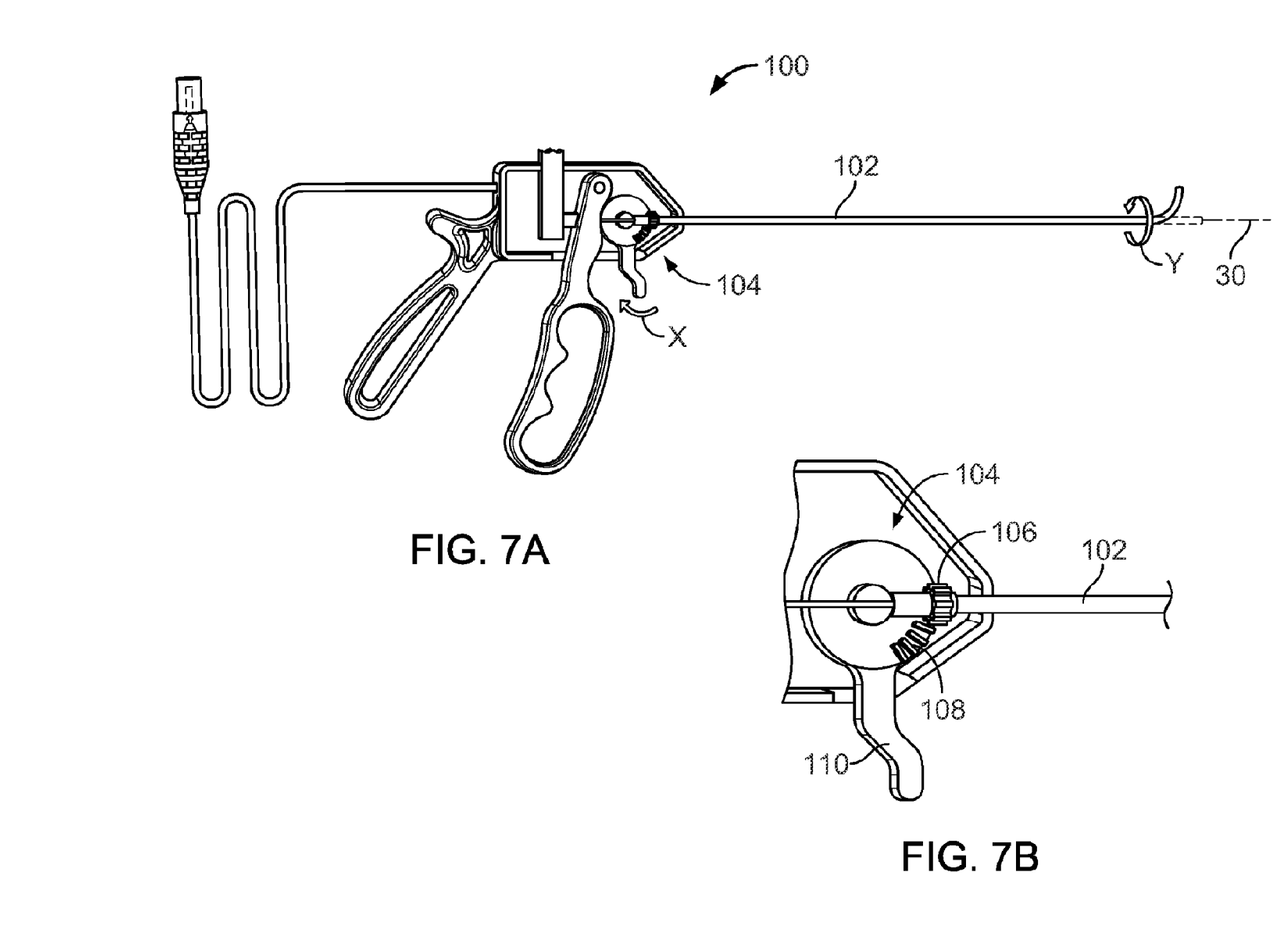
FIG. 7A is a side view of another alternative implementation of a probe with a flexible shaft.
FIG. 7B is a partial side view of the probe of FIG. 7A.

Referring to FIGS. 7A and 7B, implementations of the probe 80 (FIG. 6) can include a rotating shaft. As shown, a probe 100 has a rotating shaft 102 that couples at its proximal end to a rotation control mechanism 104. The shaft 102 and the rotation control mechanism 104 are mechanically linked such that a motion of the rotation control mechanism 104 in a direction indicated by arrow X results in a rotation of the shaft 102 about the shaft axis 30 in a direction indicated by arrow Y. For example, as shown in FIG. 7B, the rotation control mechanism 104 can include a shaft gear 106 attached to the shaft 102 and a control gear 108 attached to a trigger 110. The shaft gear 106 and the control gear 108 are mechanically engaged so as to allow the rotating motion of the shaft 102 as described above when the user actuates the trigger 110. In some cases, the shaft gear 106 and the control gear 108 can be a part of a bevel gear or other similar gear mechanisms.

Figure 8A:
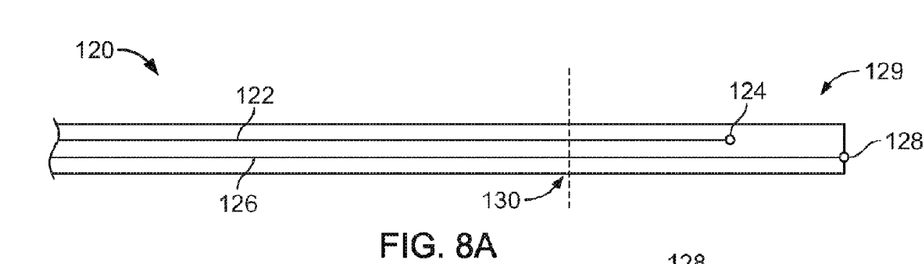
FIGS. 8A-8C are partial side views of another alternative implementation of a flexible shaft.
Figure 8B:
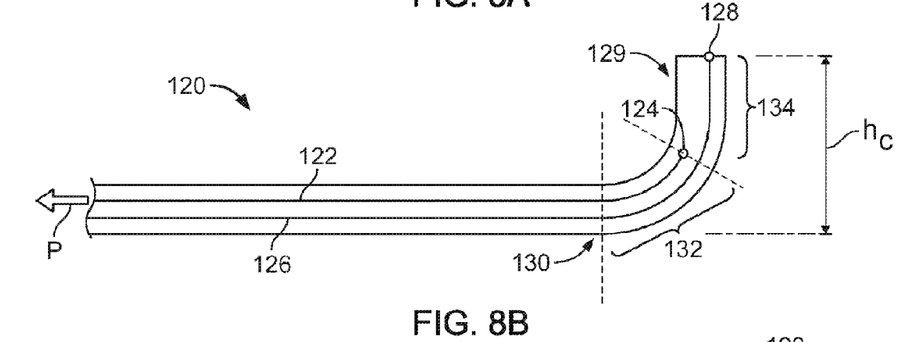
Figure 8C:
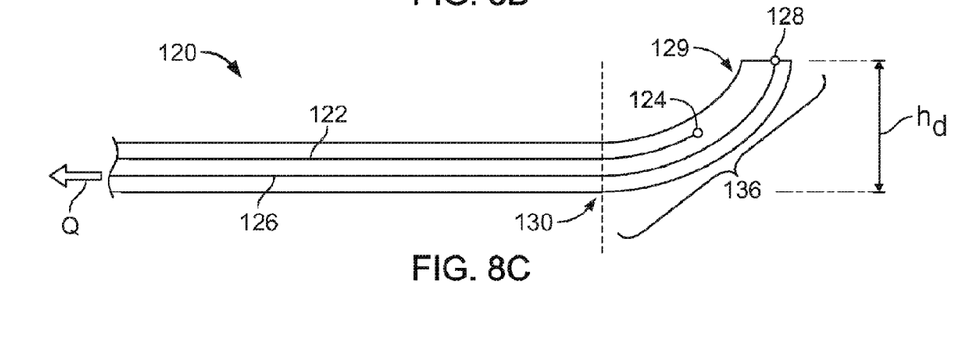

Referring to FIGS. 8A-8C, an alternative implementation of the angular control mechanism uses multiple pull wires to change the maximum radial offset of the flexible tip without changing the maximum angular orientation. As shown, a shaft 120 contains a first pull wire 122 coupled to an inner surface of the shaft 120 at a first connection site 124 and a second pull wire 126 coupled to the inner surface of the shaft 120 at a second connection site 128. The first and second connection sites 124, 128 are positioned at different locations along a length of the shaft 120 such that a bending motion caused by pulling the first pull wire 122 is different from a bending motion caused by pulling the second pull wire 126.

In the example shown in FIGS. 8A-8C, the second connection site 128 is positioned distally of the first connection site 124. In use, pulling the pull wires 122, 126 causes a distal portion 129 of the shaft 120 to bend starting from a pivot region 130 of the shaft 120. As discussed above, the pivot region 130 can be defined by a rigid member that is positioned proximally relative to the pivot region 130. Alternatively, the pivot region 130 can be defined without using the rigid member by introducing a flexible region, for example a portion of the shaft having flex cuts, that is positioned distally relative to the pivot region 130. In some implementations, both the rigid member and the flexible region can be used together to define the pivot region 130.

As shown in FIG. 8B, pulling on the first pull wire 122 in a direction indicated by arrow P causes the distal portion 129 to flex resulting in a curved region 132 between the pivot region 130 and the first connection site 124. A straight region 134 positioned between the first connection site 124 and the second connection 128 remains straight. A radial offset, $h_c$, is generated between an axis of the shaft 120 and a tip of the distal portion 129. Similarly, as shown in FIG. 8C, pulling on the second pull wire 126 in a direction indicated by arrow Q causes the distal portion 129 to flex resulting in a curved region 136 between the pivot region 130 and the second connection site 128. A radial offset, $h_d$, is generated between the axis of the shaft 120 and the tip of the distal portion 129. In the example shown, $h_c$ is greater than $h_d$ due to the presence of the straight region 134 and a radius of curvature of the curved region 132 being smaller than a radius of curvature of the curved region 136.

A constant maximum angular orientation of the distal portion 129 of the shaft 120 can be maintained, regardless of the maximum radial offset, by using an angular control mechanism having a first actuator (not shown) coupled to a proximal portion of the first pull wire 122 and a second actuator (not shown) coupled to a proximal portion of the second pull wire 126. For example, the first and second actuators can be configured or adapted such that moving the first actuator to a first end position causes the distal portion 129 to bend to the maximum offset, $h_c$, and a maximum angular orientation of, for example, approximately 90 degrees as shown in FIG. 8B. Similarly, moving the second actuator to a second end position causes the distal portion 120 to bend to the smaller maximum offset, $h_d$, and a maximum angular orientation of, for example, approximately 90 degrees as shown in FIG. 8C. Additionally, both first and second pull wires 122, 126 can be actuated simultaneously to result in additional bending configurations of the distal portion 129 of the shaft 120. In some cases, positions of the first and second connection sites 124, 128 can be translated along a length of the shaft 120 to vary, for example, the lengths and/or positions of curved regions 132, 136.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

The invention claimed is:

1. A method of controlling a shaft of an instrument, the shaft including a flexible region and being coupled proximally to an actuator, wherein a movement of the actuator causes portions of the flexible region positioned distal of a pivot region to bend, the method comprising:
moving the actuator so that a distal end of the shaft bends to a first angular orientation and a first radial offset distance;
translating a position of the pivot region from a first location along the shaft to a second location along the shaft different than the first location; and
after translating the position of the pivot region, moving the actuator so that the distal end of the shaft bends to a second angular orientation and a second radial offset distance;
wherein the first and second angular orientations are substantially equal and the first and second radial offset distances are different.

2. The method of claim 1, wherein:
moving the actuator so that the distal end of the shaft bends to the first angular orientation and the first radial offset distance comprises moving the actuator to a first end position; and
moving the actuator so that the distal end of the shaft bends to the second angular orientation and the second radial offset distance comprises moving the actuator to a second end position.

3. A method of controlling a shaft of an instrument, the shaft including a flexible region and being coupled proximally to an actuator, wherein a movement of the actuator causes portions of the flexible region positioned distal of a pivot region to bend, the method comprising:
moving the actuator so that a distal end of the shaft bends to a first maximum angular orientation and a first maximum radial offset;
translating a position of the pivot region by translating member axially along the length of the shaft; and
after translating the position of the pivot region, moving the actuator so that the distal end of the shaft bends to a second maximum angular orientation and a second maximum radial offset;
wherein the first and second maximum angular orientations are substantially equal and the first and second maximum radial offsets are different.

4. A method of controlling a shaft of an instrument, the shaft including a flexible region and being coupled proximally to an actuator, wherein a movement of the actuator causes portions of the flexible region positioned distal of a pivot region to bend, the method comprising:
moving the actuator to a first end position so that a distal end of the shaft bends to a first maximum angular orientation and a first maximum radial offset;
translating a position of the pivot region, and wherein translating the position of the pivot region to a first pivot position restricts the actuator from moving beyond the first end position; and
translating the position of the pivot region to a second pivot position restricts the actuator from moving beyond a second end position; and
after translating the position of the pivot region, moving the actuator to the second end position so that the distal end of the shaft bends to a second maximum angular orientation and a second maximum radial offset;
wherein the first and second maximum angular orientations are substantially equal and the first and second maximum radial offsets are different.

5. The method of claim 4 further comprising moving a pivot control element to translate the position of the pivot region by translating a rigid member disposed axially along the shaft and to adjust an end point of the actuator to correspond to the substantially equal maximum angular orientation of the distal end of the shaft.

6. The method of claim 1, wherein moving the actuator causes a pull wire to be pulled, the pull wire being coupled proximally to the actuator and distally to the shaft, such that pulling the pull wire causes the distal end of the shaft to bend.

7. The method of claim 1, further comprising rotating the shaft about an axis of the shaft.

8. The method of claim 1, wherein translating a position of the pivot region from the first location to the second location along the shaft further comprises translating a rigid member axially along the length of the shaft.

* * * * *